(12) United States Patent
Carr

(10) Patent No.: US 9,372,114 B2
(45) Date of Patent: Jun. 21, 2016

(54) SPECTROPHOTOMETER COMPRISING AN INTEGRATED FABRY-PEROT INTERFEROMETER

(71) Applicant: William N. Carr, Montclair, NJ (US)

(72) Inventor: William N. Carr, Montclair, NJ (US)

(*) Notice: Subject to any disclaimer, the term of this patent is extended or adjusted under 35 U.S.C. 154(b) by 0 days.

(21) Appl. No.: 14/513,669

(22) Filed: Oct. 14, 2014

(65) Prior Publication Data

US 2016/0054179 A1 Feb. 25, 2016

Related U.S. Application Data

(60) Provisional application No. 62/039,528, filed on Aug. 20, 2014.

(51) Int. Cl.
| | |
|---|---|
| *G01B 9/02* | (2006.01) |
| *G01J 3/45* | (2006.01) |
| *G01J 3/26* | (2006.01) |
| *G01J 3/10* | (2006.01) |
| *G01N 21/31* | (2006.01) |

(52) U.S. Cl.
CPC .... *G01J 3/26* (2013.01); *G01J 3/10* (2013.01); *G01J 3/45* (2013.01); *G01N 21/31* (2013.01); *G01N 2201/061* (2013.01); *G01N 2201/0636* (2013.01); *G01N 2201/12* (2013.01)

(58) Field of Classification Search
CPC ................. G01J 3/26; G01J 3/45; G01J 3/10; G01N 21/31; G01N 2201/061; G01N 2201/12; G01N 2201/0636; G02N 5/281; G02N 5/282
USPC ................................................. 356/454, 519
See application file for complete search history.

(56) References Cited

U.S. PATENT DOCUMENTS

| | | | | |
|---|---|---|---|---|
| 5,561,523 A | * | 10/1996 | Blomberg | G02B 26/001 356/454 |
| 6,339,187 B1 | | 1/2002 | Inoue | |
| 2003/0148620 A1 | * | 8/2003 | Chavan et al. | 438/706 |
| 2005/0012935 A1 | * | 1/2005 | Kersey | 356/519 |
| 2005/0109940 A1 | * | 5/2005 | Carr | 250/338.4 |
| 2005/0111008 A1 | * | 5/2005 | Murata | 356/519 |
| 2006/0066876 A1 | * | 3/2006 | Kothari | 356/519 |

(Continued)

OTHER PUBLICATIONS

"Related U.S. Appl. No. 14/676,867", "NonFinal Office Action", May 22, 2015, Publisher: USPTO, Published in: US.

(Continued)

*Primary Examiner* — Michael A Lyons
*Assistant Examiner* — Dominic J Bologna
(74) *Attorney, Agent, or Firm* — Kaplan Breyer Schwarz & Ottesen, LLP

(57) ABSTRACT

An "integrated" Fabry-Perot interferometer, such as for use in a spectrophotometer, is fabricated by attaching two micro-machined semiconductor-on-insulator wafers to one another. One mirror is formed on each micro-machined wafer. One mirror is supported by a thermally insulated, suspended micro-platform. In some embodiments, interferometer cavity length is adjustable. Detectors are disposed at least partially within the micro-platform. In some embodiments, the interferometer, a light source, and other circuitry and components, such as wireless communications components, are contained in a sealed package that includes a sampling region, thereby providing an integrated spectrophotometer. The integrated spectrophotometer can be implanted, for example, in animal tissue environments, such as for analyzing various compounds in the blood.

25 Claims, 13 Drawing Sheets

(56) References Cited

U.S. PATENT DOCUMENTS

| | | | |
|---|---|---|---|
| 2008/0062426 A1* | 3/2008 | Yoshida | 356/454 |
| 2008/0186504 A1* | 8/2008 | Kiesel et al. | 356/454 |
| 2008/0252442 A1* | 10/2008 | Mohamadi | 340/539.1 |
| 2011/0261370 A1* | 10/2011 | Floyd et al. | 356/614 |
| 2012/0109584 A1* | 5/2012 | Urushidani | G01J 3/027 702/189 |
| 2012/0162664 A1* | 6/2012 | Bakke et al. | 356/519 |
| 2012/0269228 A1 | 10/2012 | Nakamura et al. | |

OTHER PUBLICATIONS

"Notice of Allowance dated Sep. 4, 2015", issued in related U.S. Appl. No. 14/676,867.

* cited by examiner

SPECTROPHOTOMETER COMPRISING AN INTEGRATED FABRY-PEROT INTERFEROMETER

FIELD OF THE INVENTION

The present invention pertains to spectrophotometers.

BACKGROUND OF THE INVENTION

Spectrophotometry is the quantitative measurement of the reflection or transmission properties of a material as a function of wavelength. Spectrophotometry is commonly used to measure the transmittance or reflectance of solutions, transparent or opaque solids, or gases. The device that performs this measurement is known as a "spectrophotometer".

FIG. 1 depicts a block diagram of a typical prior-art spectrophotometer 108 in use performing a spectral assay of media 104. Spectrophotometer 108 includes Fabry-Perot interferometer 112, detector(s) 116, and processor 120.

Interrogating light 102 emitted from broadband light source 100 is directed towards media 104. The light is dispersed, via reflection, absorption, etc., as it passes through media 104. The dispersion alters the spectral content of the interrogating light. The specifics of the alteration depend on and can be characteristic of media 104. As a consequence, analysis of spectrally altered light 106 can provide information about media 104. This information is "extracted" using interferometer 112, detector(s) 116, and processor 120, as discussed further below.

Spectrally altered light 106 enters Fabry-Perot interferometer 112. Wavelengths of spectrally altered light 106 that resonate within interferometer 112 form filtered exit light 110. In this fashion, interferometer 112 selectively filters spectrally altered light 106.

Filtered light 110 exits interferometer 112 and is directed to detector(s) 116. In some prior-art spectrophotometers, detector(s) 116 are sensitive to certain wavelengths of electromagnetic (EM) radiation and generate electrical signals 118 (i.e., a photocurrent) when such wavelengths are detected. The amplitude of signals 118 is indicative of the light intensity at the particular wavelength. Signal(s) 118 from detector 116 are conditioned (analog-to-digital conversion, etc.) and transmitted to processor 120. In the processor, signal(s) 118 are processed via a Fourier transform or related algorithms to provide assay 124 of the spectral content of filtered exit light 110.

As previously noted, filtered exit light 110 will contain wavelengths corresponding to the resonances of the interferometer cavity. Analysis of those particular wavelengths will rarely provide a complete spectral analysis of spectrally altered light 106. Consequently, as part of the spectrophotometry process, the resonant wavelengths of interferometer 112 are altered. In some spectrophotometers, this alteration is implemented by changing the cavity length of the interferometer, such as via cavity-length controller 114. Each such alteration will change the spectral content of exit light 110. In this fashion, a wavelength sweep is performed, wherein for each change in cavity length (and, hence, spectral content of the exit light 110), the detection operation is repeated. This ultimately provides a complete spectral analysis of media 104 (assuming that the frequency sweep is large enough). The spectral analysis, which provides light intensity as a function of wavelength, can be used as a fingerprint (for identification purposes) and/or as a means to quantify the amount of media that is present. Identification and/or quantification involves a comparison of the spectral analysis to a database that provides compound identification as a function of spectrum or concentration (of a particular media) as a function of spectrum.

An embodiment of conventional Fabry-Perot interferometer 112 is depicted in FIG. 2. Interferometer 112 consists of two spaced-apart mirrors 226 and 228. The mirrors are typically "highly" reflective, such that most of the light impinging on them is reflected. The change in the "thickness" of the lines that are representative of light "beam" is intended to be (qualitatively) indicative of the attenuation of the transmitted intensity resulting from reflections at mirror surfaces.

The portion of light 106 entering interferometer 112A makes multiple (partial) reflections between mirrors 226 and 228. Although depicted as a single coherent beam (like a laser beam), spectrally altered light 106 is in the form of a broad plane wave comprising multiple wave fronts. Constructive interference (resonance) occurs if the transmitted light is in phase, and this corresponds to a high-transmission peak of the interferometer. If the transmitted light is out-of-phase, destructive interference occurs and this corresponds to a transmission minimum.

The resonant wavelengths of a Fabry-Perot interferometer are a function of the angle that light travels through the interferometer, the size of gap between the mirrors (i.e., cavity length) and the refractive index of the medium between mirrors. For fixed values of those parameters, the wavelength of the reflected light determines whether that light is "in phase" or "out-of-phase".

The resonant wavelengths of a Fabry-Perot interferometer can be altered by changing its cavity length. Cavity length can be changed via cavity-length controller 114 (see FIG. 1), which in interferometer 112 depicted in FIG. 2 comprises electrostatic actuator 230.

Electrostatic actuator 230 includes controlled voltage source 232. Mirrors 226 and 228 are electrically conductive, so that when a voltage is applied across them, an electrostatic force of attraction results. Mirror 226 is suspended (e.g., from a stationary substrate, etc.) via tethers 234 that enable mirror 226 to move. Consequently, when a voltage is applied across mirrors 226 and 228 creating an electrostatic force of attraction, tethered mirror 226 moves toward mirror 228. This movement reduces the size of gap G compared to the quiescent state in which no voltage is applied. Within the range of movement of mirror 226, the size of gap G is a function of voltage. Since, as already indicated, a change in cavity length alters the resonances of the interferometer, the transmission spectrum as a function of wavelength for interferometer 112 can be altered via electrostatic actuator 230.

Most prior-art spectrophotometers are fabricated with minimal integration of elements. This affects cost and also limits the type of applications in which such spectrophotometers can be used.

SUMMARY OF THE INVENTION

Embodiments of the present invention provide a highly integrated Fabry-Perot interferometer and a highly integrated spectrophotometer.

In some embodiments, the invention provides an "integrated" Fabry-Perot interferometer with an adjustable cavity length. The integrated interferometer includes (in addition to the interferometer itself), one or more actuation structures for controlling cavity length and one or more detectors.

In the illustrative embodiment, the integrated interferometer is fabricated by attaching two micro-machined semiconductor-on-insulator wafers to one another. One mirror is formed on each such wafer. In the illustrative embodiment, one of the wafers is machined to provide a thermally insulated, suspended "micro-platform" comprising at least a layer of single crystal silicon. The micro-platform supports one of the two interferometer mirrors. Detectors are formed at least partially within the micro-platform. In the illustrative embodiment, the detectors are thermal detectors. Very small electrical conductors, referred to herein as "nanowires," which can form part of the detectors, provide electrical connection between the micro-platform and "off-platform" electrical contacts, located elsewhere in the interferometer, for extracting the detector signals for processing. The nanowires are also used for applying a voltage across the mirrors for electrostatic control of interferometer cavity length.

In some alternative embodiments, rather than having an adjustable cavity length, an interferometer in accordance with the present teachings includes multiple cavities, each having a different fixed cavity length.

In some embodiments, the integrated Fabry-Perot interferometer forms part of a spectrophotometer. In addition to the interferometer, the spectrophotometer includes hardware/software for processing the signals generated by the detectors of the interferometer.

In some embodiments, the spectrophotometer also includes one or more of: a light source, a region for receiving an analyte of interest, a means of calibration, and a power supply (optionally energy-harvesting). In embodiments that include a light source and power supply, the spectrophotometer can be contained within a sealed package and configured for remote wireless (e.g., RFID, etc.) operation. Remote operation enables, for example, implanting the spectrophotometer in animal tissue environments, such as for analyzing various compounds in the blood.

Embodiments of the spectrophotometer can be used, for example, to determine the identity of a compound (e.g., glucose, oxygen, markers, etc.) and its concentration in a media (e.g., blood or other fluid, etc.). This is accomplished, for example, by comparing measurements obtained by the spectrophotometer to a reference file for the compound. The reference file includes information such as the wavelength spectrum of the compound, intensity-versus-wavelength values for the compound at varying concentrations, and the like.

As previously noted, in some embodiments, an integrated spectrophotometer is provided. The integrated spectrophotometer is physically adapted to be implanted within animal tissue, including a human body (earlobe, finger, or skin flap, etc.) to provide an assay of one or more of glucose, oxygen, and other analytes in body fluid. Physical adaptations for such applications include, without limitation, an ability to transmit data and/or receive power wirelessly.

In some other embodiments, the spectrophotometer is used in non-biological applications, such to analyze feed and effluent streams for laboratory chemical reactors or analytical instruments, and can even be used within such reactors and instruments. The spectrophotometer can be configured for placement in chemical production facilities to detect leaks and products of chemical reactions. The spectrophotometer can be configured for placement down-hole with petroleum exploratory drilling rigs for the purpose of analyzing a liquid or gas. This enables in-situ analysis without having to extracting the liquid/gas to the surface.

The spectrometer can be used with sources of electromagnetic energy such as sunlight, emissions from an explosion or combustion event, blackbody emissions from a remote scene, or modulated signal beams. Consequently, embodiments of the spectrophotometer can configured to detect and analyze spectral components of light created during explosions, including detection of toxic gases. The spectrophotometer can be configured to monitor absorption spectra of sunlight as filtered by a media, such as smokestack effluents, thereby monitoring, for example, coal ash and the like. In some embodiments, the spectrophotometer can be configured for analyzing multiple infrared wavelengths so as to monitor the "blackbody" emission spectrum from remote scenes and objects to determine the surface temperature thereof.

The spectrophotometer can be configured for hand-held use thereby providing a highly mobile unit enabling movement and placement not previously practical with many prior-art spectrophotometers.

DETAILED DESCRIPTION

Definitions

The following terms are explicitly defined for use in this disclosure and the appended claims:
  "infrared" refers to the broad range of photon wavelengths in the range from visible light at 700 nm to 100 microns, including the NIR, Mid-IR, LWIR, and ULWIR wavelength bands.
  "micro-platform" means a patterned layer having dimensions of about 100 nanometers on a side up to about 1 centimeter on a side.
  "nano-dimensioned" or "nano-sized" or "nanometer sized" means a structure whose controlled dimension is less than 1 micron (1000 nanometers).

"nanowires" are very small (nano-dimensioned) electrically conductive elements. Although nanowires can include metallization (they could alternatively be appropriately doped to provide electrical conductivity), the structure thereof is based on a non-metallic material, such as a semiconductor or electrically insulating material.

"quiescent state" means a non-actuated or non-energized state.

"RFID" refers to a two-way wireless communications protocol.

"Semiconductor-on-insulator" refers to a wafer typically having a three layers including an "active" layer, a "buried oxide layer" ("box") layer, and a "handle" layer. The box layer is sandwiched by the active and handle layers. The most common semiconductor-on-insulator wafer has traditionally included a silicon device layer, a silicon dioxide box layer, and a silicon handle. This wafer is usually referred to as an "SOI" wafer. More recently, semiconductor-on-insulator wafers including: silicon-germanium alloy/silicon oxide/silicon handle, germanium/silicon oxide/silicon handle, and other combinations including various semiconductors and dielectric films are now available.

"supported by" means that, for example, one layer is supported by, but not necessarily disposed on, another layer. For example, if a third layer is disposed on a second layer that is, in turn, disposed on a first layer, the third layer is "supported by" (but not "disposed on") the first layer.

Figure 1:
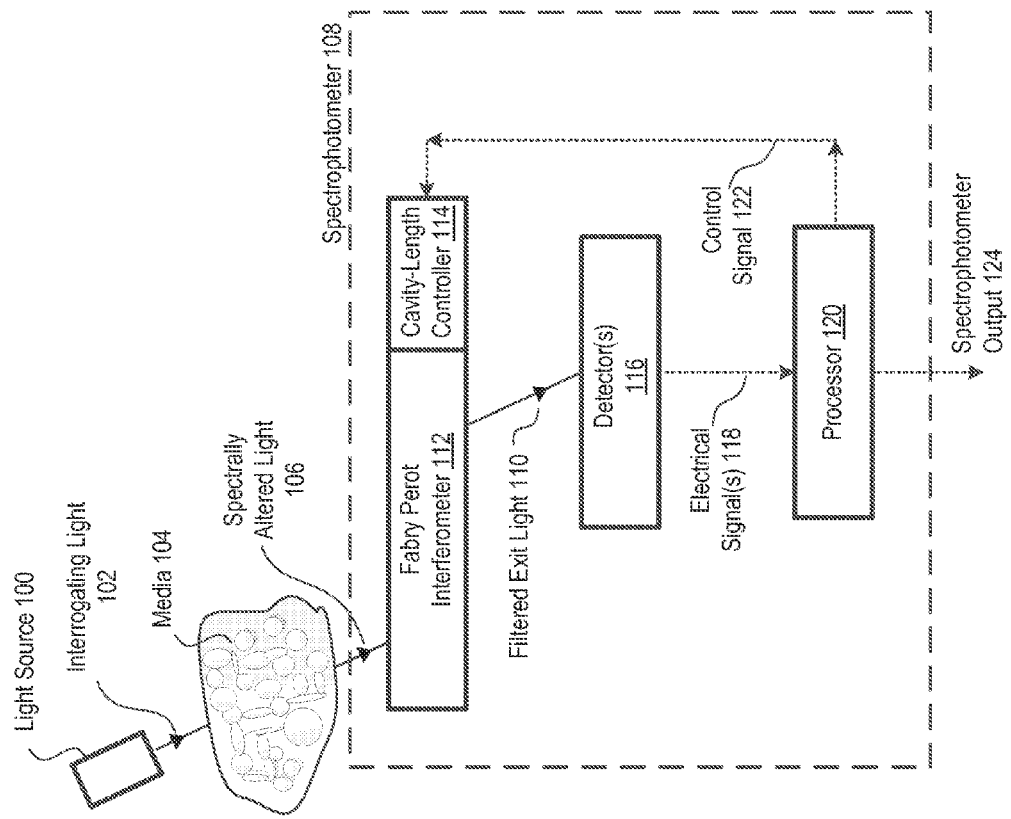
FIG. 1 depicts a prior-art spectrophotometer including a conventional Fabry-Perot interferometer configured with discrete components.
Figure 2:
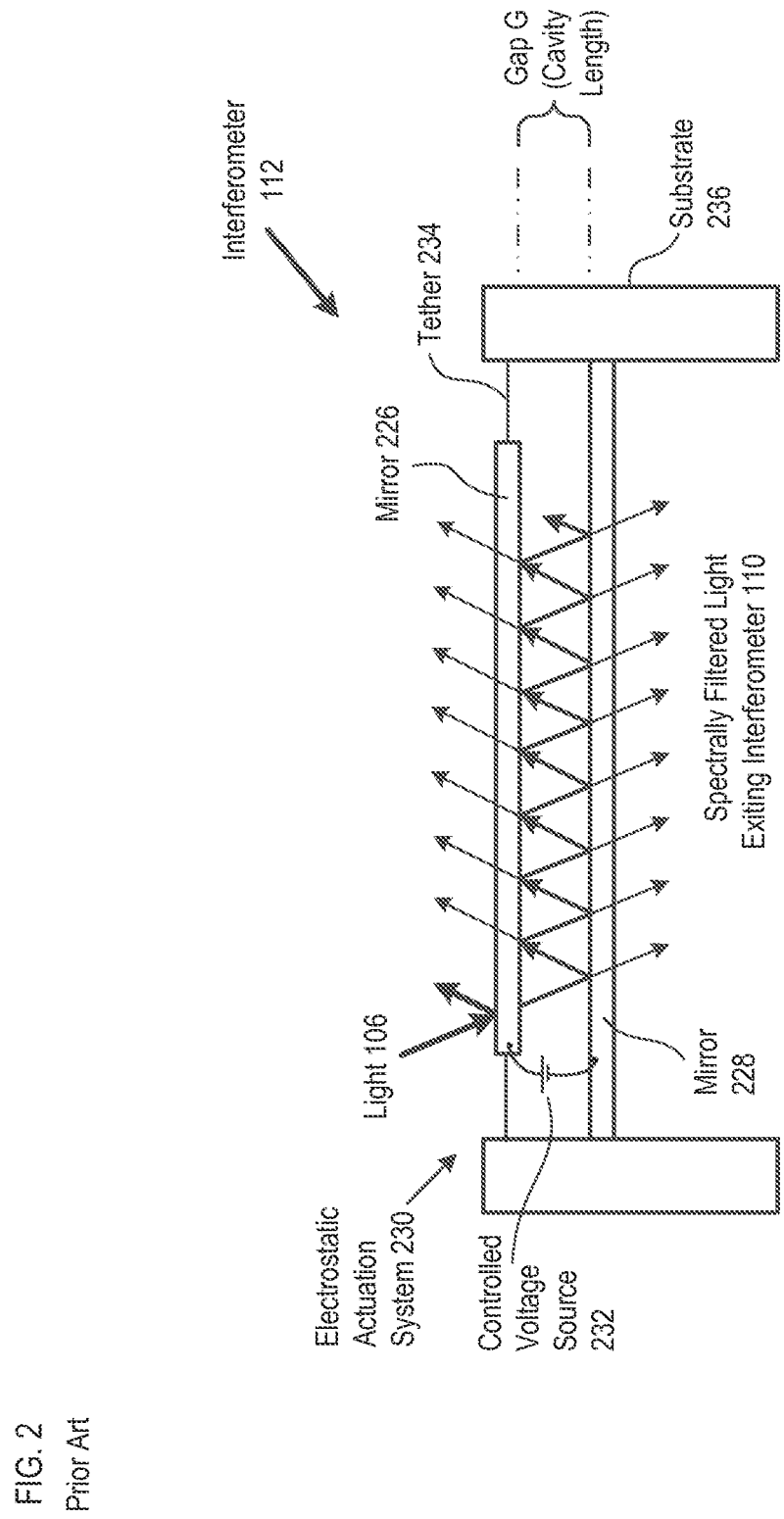
FIG. 2 depicts a conventional Fabry-Perot interferometer.
Figure 3:
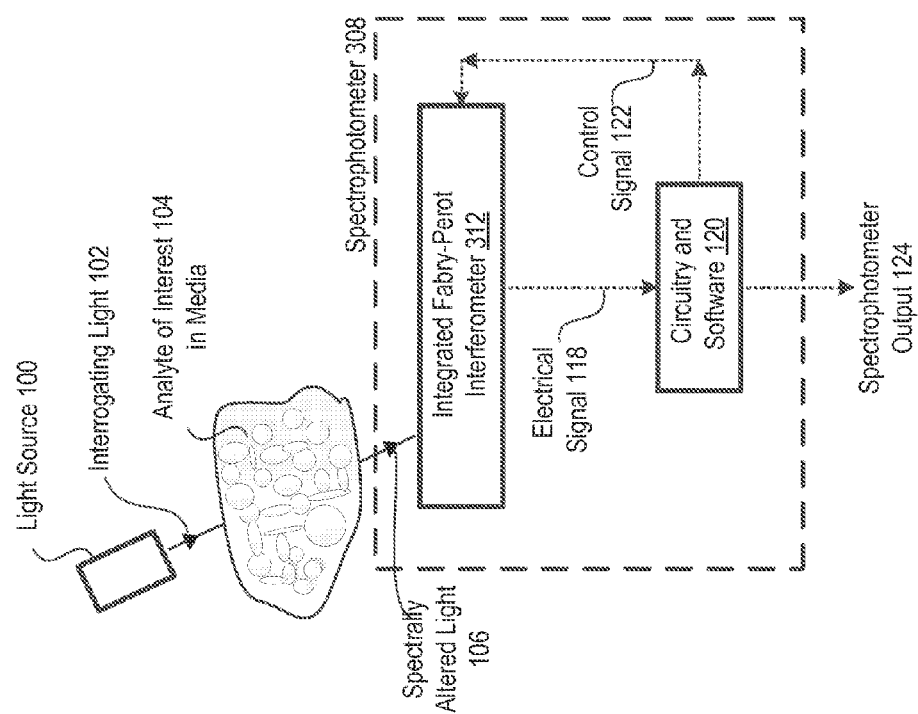
FIG. 3 depicts a spectrophotometer including an integrated Fabry-Perot interferometer in accordance with an illustrative embodiment of the present invention.

FIG. 3 depicts the salient features of spectrophotometer 308 in accordance with the present teachings. The spectrophotometer includes integrated Fabry-Perot interferometer 312 and electronic digital and analog circuitry and software 120.

In operation, Interrogating light 102 is emitted from light source 100. Light source 100 can be a broad-band or narrow-band source of light for emitting wavelengths of interest, including visible and infrared light, as a function of the analyte being interrogated. Light source 100 can be, without limitation, an LED, a quantum cascade laser, or a heated blackbody including environmental sunlit scenes.

Interrogating light 102 is passed through analyte 104, which is at least partially transparent. More precisely, the analyte is typically not transparent. However, in such cases, it is usually dispersed within a transparent or partially transparent media, such as blood, water, other liquids, gases, etc. The spectral content of interrogating light 102 is altered by virtue of passing through the analyte, resulting in spectrally altered light 106. This spectral alteration is due to the absorption and/or dispersion of certain wavelengths of the interrogating light. Spectrally altered light 106 is directed into integrated Fabry-Perot interferometer 312.

Figure 5:
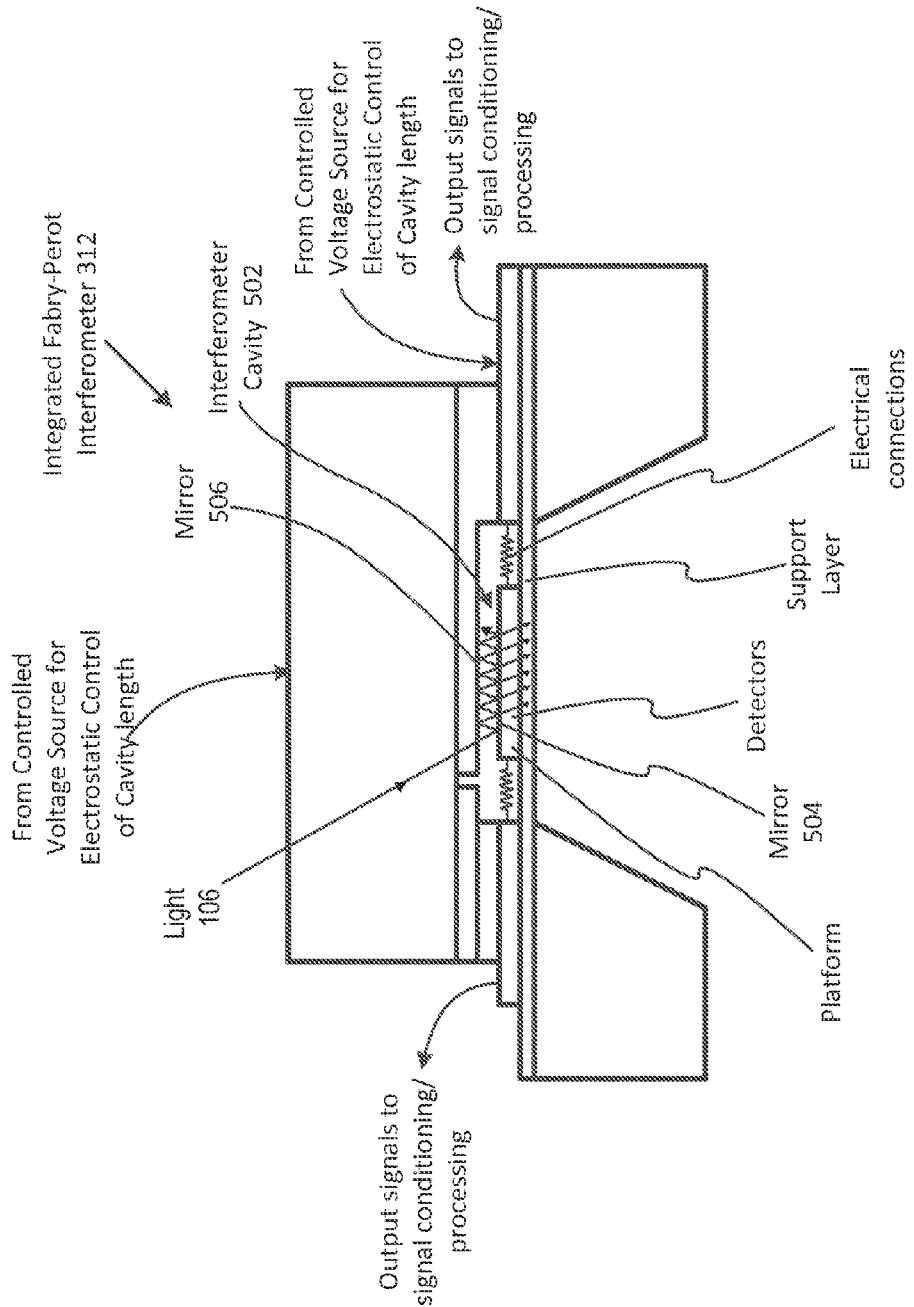
FIG. 5 depicts an integrated Fabry-Perot interferometer in accordance with a first illustrative embodiment of the present invention.

With continued reference to FIG. 3 and now referring to FIG. 5, integrated Fabry-Perot interferometer 312 includes two partially and highly reflective mirrors 504 and 506. Cavity 502 is defined between the mirrors; the length of cavity 502 is the size of the gap between the two mirrors. Mirror 504 is disposed on a platform that resides on a suspended support layer. As a consequence of this arrangement, mirror 504 is movable. On application of a voltage across mirrors 504 and 506, which results in an electrostatic force-of-attraction, the platform and mirror 504 move towards mirror 506. This alters the gap between the mirrors (i.e., alters the length of cavity 502 of interferometer 312). In this context, the mirrors must be electrically conductive. More precisely, either the mirrors, or a layer associated therewith, must be electrically conductive. Thus, as used herein, the term "electrically conductive," when used to describe a mirror or a highly-reflective surface, means that the either the mirror/surface or something attached to it is electrically conductive.

The light is spectrally filtered in Fabry-Perot interferometer 312 in conventional fashion. As mentioned in the Background section, the filtering is a function of the resonant wavelengths of the interferometer and those resonances are a function of interferometer cavity length, among other parameters. Although the spectral filtering is dependent on other parameters as previously mentioned, it is cavity length that is varied in the illustrative embodiments.

The spectrally filtered light exiting interferometer cavity 502 through mirrors 504 and 506 passes into adjacent layers of material. Light passing through mirror 504 enters the platform, which contains detectors. In the illustrative embodiment, the detectors are thermocouples that are series connected to form a thermopile. The filtered light raises the temperature of the platform above that of the surrounding layer. As a consequence, a (Seebeck) voltage is generated, in known fashion, from the thermocouple array. The thermal detectors operate in analog fashion; that is, the amplitude of the voltage generated is proportional to the power absorbed by the platform from the light. Thus, the amplitude of the voltage is a function of the light intensity at a particular wavelength. The first mirror on the micro-platform is electrically connected by nanowires to an aluminum interconnect patterned on the first silicon substrate.

Cavity length is periodically changed to alter the resonant frequencies of interferometer 312. As previously noted, cavity length is changed electrostatically by applying a voltage across the mirrors. The voltage is applied via a controlled voltage source. For each such periodic change, signal voltages are generated by the detectors.

The relationship between the applied voltage and the wavelengths of the light exiting the interferometer can be determined in known fashion. Using that relationship, in conjunction with the amplitude of the voltage generated by the detectors during each period, information concerning light intensity as a function of wavelength can be obtained.

The detector signals 118 are transmitted off-platform to electrical contacts situated elsewhere in the interferometer. From these contacts, signals 118 are transmitted to electronic circuitry 120 (external to the interferometer). Electronic circuitry 120 includes, without limitation, signal conditioning (reduce noise), an analog-to-digital converter, a suitably programmed processor, processor-accessible memory, and wires for conducting electrical signals to and from various components/structures of integrated Fabry-Perot interferometer 312. The processor includes, without limitation, algorithms for processing the detector signals, such as via a Fourier transform or variations thereof, algorithms for controlling and varying the cavity length, and, optionally, algorithms for comparing the processed information with reference information about the analyte that is stored in the processor-accessible memory. In this fashion, a complete spectral assay of the light that resulted from interrogation of the analyte is obtained and can be used to determine qualitative and quantitative information about the analyte.

Further detail of an embodiment of integrated Fabry-Perot interferometer 312 is provided later in this specification in conjunction with FIGS. 6A, 6B, 7, 8A, and 8B.

FIG. 5 depicts light 106 entering interferometer 312 via "upper" mirror 506. Those skilled in the art will appreciate that light 106 could also (or alternatively) enter interferometer 312 through "lower" mirror 504 and be processed in essentially the same fashion.

In spectrophotometer 308, neither light source 100 nor electronic circuitry 120 is co-located in a housing with integrated Fabry-Perot interferometer 312.

Figure 4:
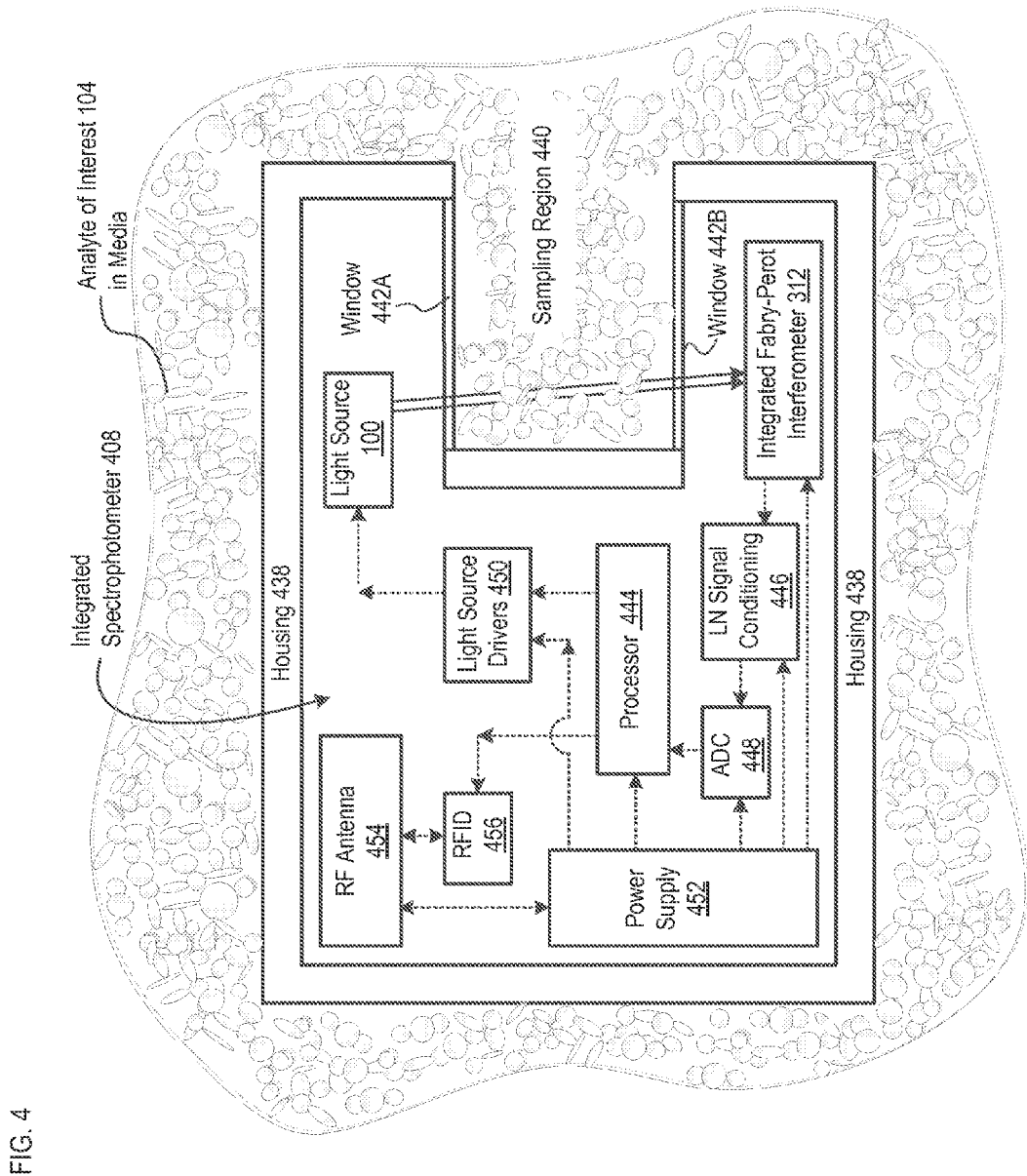
FIG. 4 depicts an integrated spectrophotometer in accordance with an illustrative embodiment of the present invention.

In accordance with some embodiments of the invention, a fully integrated spectrophotometer is provided. An embodiment of fully integrated spectrophotometer 408 in accordance with the present invention is depicted in FIG. 4.

Fully integrated spectrophotometer 408 includes housing 438 that hermetically seals its contents, including light source 100, integrated Fabry-Perot interferometer 312, and various electronic devices and circuitry (e.g., processor 444, low-noise signal conditioning 446, analog-to-digital conversion 448, light source drivers 450, power supply 452, RF antenna 454, and RFID transponder 456).

Housing 438 is configured to provide sampling region 440. The sampling region is defined in a region that is external to housing 438 and is thus exposed to the ambient environment. In the illustrative embodiment, sampling region 440 is formed by creating an "inlet" wherein the walls of the housing extend inwardly for a distance. This inlet has a "u" shape, wherein the two "legs" of the "u" are windows 442A and 442B. The windows are leak proof and transparent to the interrogating light emitted from light source 100. As depicted in FIG. 4, when spectrophotometer 408 is placed in a fluid, the fluid readily enters sampling region 440. In operation, light from light source 100 is directed through window 442A to sampling region 440, which contains an analyte of interest.

The interrogating light passes through the media containing the analyte in sampling region 440 and is spectrally altered as previously discussed. The spectrally altered light then re-enters housing 438 through second window 442B. In the illustrative embodiment, integrated Fabry-Perot interferometer 312 is situated behind window 442B, so that the spectrally altered beam passes through that window and into the interferometer.

The spectrally altered beam is spectrally filtered in interferometer 312 in the manner previously discussed. The output from the detectors is extracted from interferometer 312 and is transmitted to low-noise signal conditioning circuitry 446 and then to analog-to-digital convertor circuitry 448. The resulting digital signal is then sent to processor 444.

In some embodiments, the processor includes processor-accessible memory containing software for controlling and varying the cavity length, software for controlling light-source drivers 450, and software for controlling communications and power functions. In such embodiments, the minimally processed data is transmitted from integrated spectrophotometer 408 to an external processor. The external processor generates the spectral assay, etc., via Fourier-transform processing or variations thereof. The external processor also compares the spectral assay to reference information, such as for qualitative (analyte identification) or quantitative (analyte concentration) determinations.

In some other embodiments, processor 444 can generate the spectral assay and, optionally, the qualitative and quantitative determinations.

In the illustrative embodiment, spectrophotometer 408 receives power and communication control through integral antenna 454 that is sensitive to electromagnetic or magnetic fields sourced from an external RFID interrogator. In the illustrative embodiment, spectrophotometer 408 includes passive RFID transponder 456 that communicates with the external interrogator by wireless means through antenna 454. The implementation of passive RFID transponder 456 is within the capabilities of those skilled in the art.

In some embodiments, spectrophotometer 408 can be powered with energy harvested from remote electromagnetic or magnetic field sources at RF wavelength bands including low frequency, high frequency, or ultra-high frequency and communicated using a wireless telemetry link. In some such embodiments, antenna 454 is operated as a "rectenna," which is a portmanteau word meaning "rectifying antenna". A rectanna is an antenna that is used to convert incident electromagnetic or magnetic energy into direct current. In its simplest form, the rectanna is implemented by connecting an RF diode connected across the dipole elements of antenna 454. The diode rectifies the AC voltage induced in the antenna to produce DC power. In such an embodiment, "power supply 452" is an appropriately connected RF diode and a capacitor for energy storage.

FIGS. 6A, 6B, 7, and 8A-8B depict further detail of an embodiment of integrated Fabry-Perot interferometer 312.

The inventor recognized that it is particularly advantageous to fabricate some embodiments of integrated Fabry-Perot interferometer 312 (as well as embodiments of other versions of the interferometer disclosed later in this specification) using semiconductor-on-insulator wafers. In particular, the alternating layer structure, the thickness of the layers, as well as the material characteristics thereof in such wafers are well suited for fabricating at least some embodiments of an integrated Fabry-Perot interferometer in accordance with the present teachings.

Figure 6A:
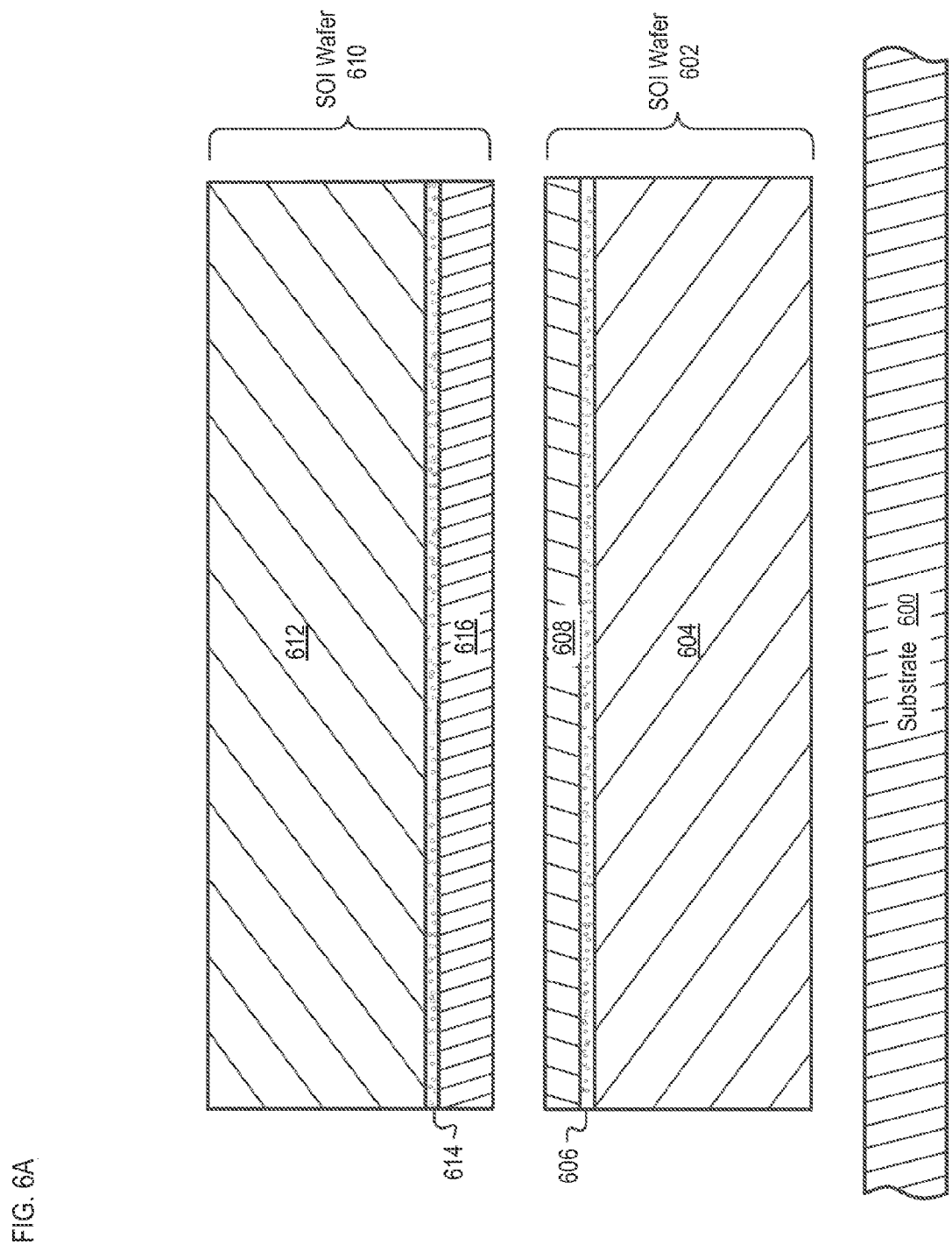
FIG. 6A depicts starting semiconductor-on-insulator wafers for fabricating the integrated Fabry-Perot interferometer in accordance with an illustrative embodiment of the present invention.
Figure 6B:
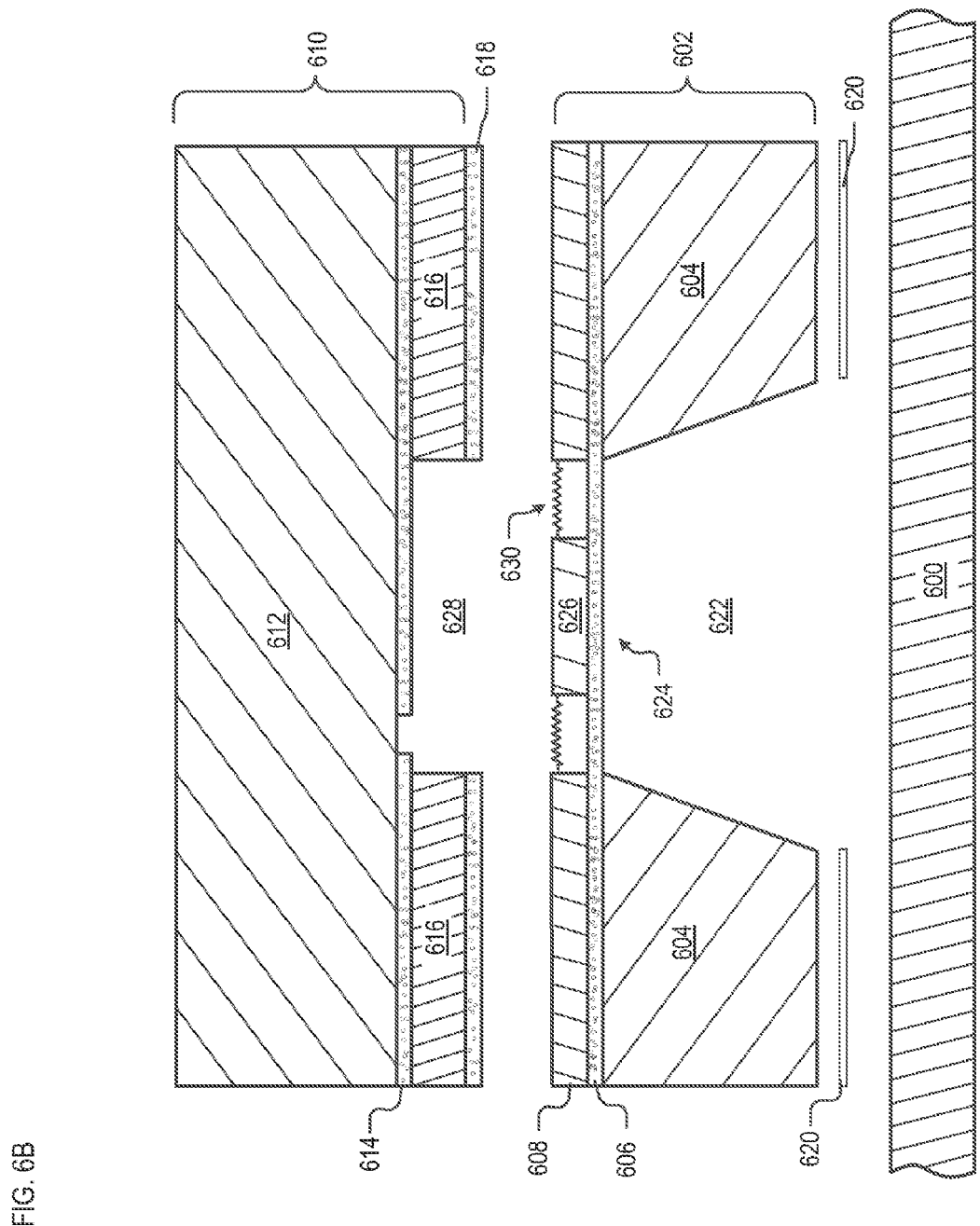
FIG. 6B depicts the starting wafers of FIG. 6A partially patterned.
Figure 7:
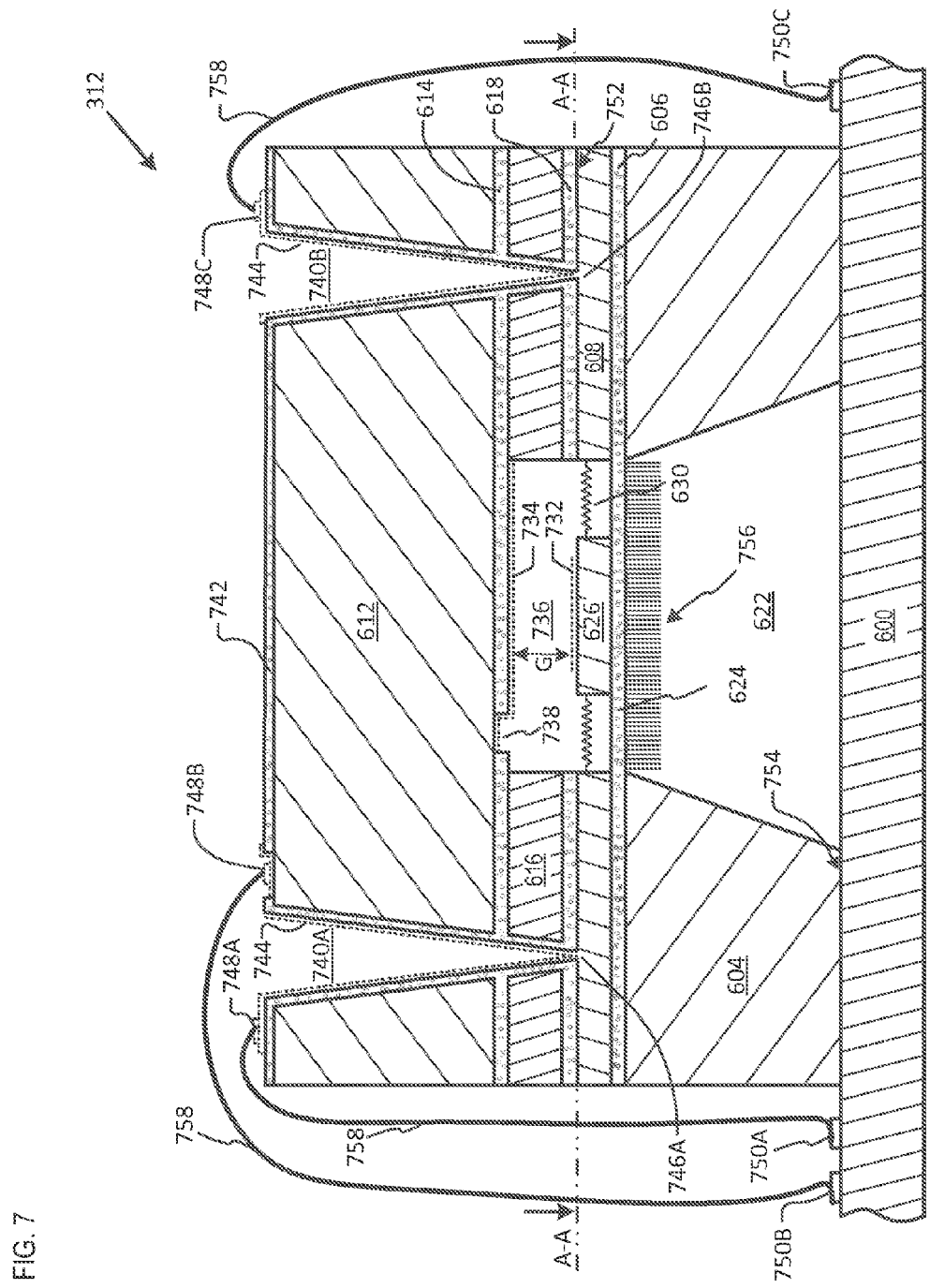
FIG. 7 depicts further detail of an embodiment of the integrated Fabry-Perot interferometer of FIG. 5 utilizing the wafers of FIGS. 6A and 6B.

As will be appreciated by comparing FIGS. 6A, 6B, and 7, in the illustrative embodiment, integrated Fabry-Perot interferometer 312 is formed from two semiconductor-on-insulator wafers 602 and 610 as well as non-electrically conductive substrate 600. FIG. 6A depicts starting wafers 602 and 610 prior to any patterning steps. During fabrication, various additional layers of material are formed on one or both of the wafers. FIG. 6B depicts wafers 602 and 610 after some patterning has been completed.

The illustrative embodiments disclose the use of silicon-on-insulator wafers, which have a device layer of single crystal silicon, a box layer of silicon dioxide, and a handle layer of silicon. Suitable semiconductor-on-insulator wafers for use in conjunction with the present invention are not limited to such silicon-on-insulator wafers. In some other embodiments, the device layer is an alloy film of silicon-germanium. Silicon-germanium offers advantages for the device layer; in particular, it has lower thermal conductivity than silicon. This is particularly useful for embodiments in which the detectors operate as thermal detectors (bolometers), since the region in which detectors reside should be thermally insulated from sources of heat other than what is delivered from the electromagnetic radiation exiting the interferometer cavity. In further embodiments those skilled in the art can easily recognize that other semiconductor-on-insulator starting wafer combinations also offer potential advantages. For instance, a wafer with a device layer of bismuth telluride or derivatives thereof can offer an increased Seebeck sensitivity compared with silicon or silicon-germanium.

Semiconductor-on-insulator wafers 602 and 610 includes three layers: a "device" layer of silicon, a buried oxide ("box") layer of silicon dioxide, and a "substrate" or "handle" layer of silicon. In wafer 602, those layers are: layer 608 (device layer), layer 606 (box layer), and layer 604 (handle layer). In wafer 610, those layers are: layer 616 (device layer), layer 614 (box layer), and layer 612 (handle layer).

Typically, the device layer is single crystal silicon (about 10-2000 nanometers in thickness), the box layer is $SiO_2$ (about 0.5 to 4 microns in thickness) and the handle layer is single crystal silicon (>250 microns in thickness). As discussed later in further detail, in some embodiments, layer 608 of wafer 602 comprises high resistivity silicon that is doped appropriately during processing.

As depicted in FIG. 6B, a portion of device layer 608 of wafer 602 is patterned to form micro-platform 626. The portion of layer 606 immediately surrounding micro-platform 626 is patterned to create structures 630, referred to herein as "nanowires," which will ultimately function as electrically conductive wires for conducting electrical signals to and from micro-platform 626. They are referred to as "nanowires" because at least the controlled dimension thereof is less than 1 micron, such as the width of nanowire 630. The portion of handle layer 604 below micro-platform 626 and nanowires 630 is removed, thereby creating region 622. This "releases" the portion of box layer 606 below micro-platform 626 and nanowires 630 such that the released portion is not supported by any underlying material. The unsupported portion of layer 606 is designated "support layer 624".

FIG. 6B depicts an additional layer 618 of electrically insulating material formed on active layer 616 of wafer 610. In the illustrative embodiment, layer 618 is a layer of silicon dioxide. A portion of layer 618 and a portion of layer 616 are removed, forming cavity 628. Wafers 602 and 610 are aligned so that "device" layers 608 and 616 are facing one another and micro-platform 626 is approximately centered with respect to cavity 628 of wafer 610. The two wafers are bonded together at layers 608 and 618 via solder or epoxy preforms 620 or direct wafer-to-wafer bonding. Wafer 602 and substrate 600 are bonded together via solder or epoxy preforms. Substrate 600 can be ceramic, quartz, or other suitable, non-electrically conductive material. Additional layers (metallization and/or insulator) may be grown/deposited on the various exposed layers of wafers 602 and 610. Such details and further description of the fabrication process is provided later in this specification.

FIG. 7 depicts further detail of an embodiment of interferometer 312. It will be apparent that the basic structure of interferometer 312 results from joining wafers 602 and 610 to one another (at interface 752) and from joining wafer 602 to substrate 600 at interface 754. The structure of integrated interferometer 312 provides optical filtering, detection, and electrical connectivity, as previously discussed and as discussed further below.

Optical Filtering.

Interferometer 312 includes highly (but partially) reflective surfaces 732 and 734. These reflective surfaces are implementations of mirrors 504 and 506 (FIG. 5). In the illustrative embodiment, reflective surfaces 732 and 734 are aluminum having a thickness in the range of about 10 to 100 nanometers. In other embodiments, materials such as gold, silver, copper, etc., and combinations thereof can be used. In yet further embodiments, the reflective surfaces can be multi-layer dielectric sandwiches of appropriate thickness. In still further embodiments, the reflective surfaces can be combinations of metals and dielectrics. The fabrication of mirrors is within the capabilities of those skilled in the art. The space between highly reflective surfaces 732 and 734 defines optical cavity 736. The length of optical cavity 736 is equal to gap G.

Detection.

Micro-platform 626 is an effectively isothermal region comprising materials suitable for (1) absorbing radiation in the visible and/or IR band and (2) for detecting such radiation. Micro-platform is effectively isothermal because the layer from which it is formed (layer 608) has high thermal conductivity and for the most part, micro-platform 626 is isolated from other layers. To detect radiation, micro-platform 626 includes detectors. In the illustrative embodiment, the detectors are embodied as thermal detectors; in particular, thermocouples. The portion of the thermocouple positioned within micro-platform 626 becomes the heated end; the other end of each thermocouple is located in the "field" region of layer 608, which is not heated and therefore provides a reference temperature.

Operating in Seebeck thermovoltaic mode, the thermocouples generate a voltage proportional to the temperature difference between micro-platform 626 and surrounding field region of layer 608. Thus, the voltage generated is proportional to the power absorbed from the light exiting the reflective surface 732.

In some other embodiments, the detectors are embodied as thermistors, and in some further embodiments, the detectors are embodied as band gap detectors. The detectors are described in further detail in conjunction with FIGS. 8A and 8B.

In some embodiments, interferometer 312 includes infrared (IR) absorber 756 for enhanced absorption of infrared radiation. IR absorber 756 is disposed on the "underside" of support layer 624. In the illustrative embodiment, IR absorber 756 is a dense grouping of individual structures having a relatively high length to width (or diameter) ratio. Such an absorber is particularly effective for enhancing the absorption of mid- to long-wave IR.

In some embodiments, IR absorber 756 is implemented as silicon structures (e.g., pedestals, etc.) referred to herein as "silicon grass". The spacing between adjacent "blades" of silicon grass is the range of nanometers. The silicon grass is not necessarily uniform in structure. The presence of the silicon grass greatly increases the absorption efficiency of IR, as opposed to an un-patterned layer of the same material. In some embodiments, the "height" of the silicon grass is at least one-quarter wavelength of the incident IR. Since the shortest wavelength IR is about 700 nanometers, this equates to a minimum height for the grass of about 175 nanometers. Typical width or diameter of the silicon grass is in the range of about 1-10 nanometers, giving a minimum L/D greater than 15 and a typical L/D in excess of 100. Silicon grass can be formed, for example, using DRIE (deep reactive ion etching).

In some further embodiments, IR absorber 756 is implemented as vertical multiwall carbon nanotubes. This can be accomplished, for example, by a first atomic layer deposition, which serves as a catalyst for growth. This deposition is followed by chemical vapor deposition ("CVD") process with an acetylene precursor to grow the VMWCNTs. The L/D for the VMWCNTs can be tens of thousands.

Electrical Connectivity.

Interferometer 312 is able to: (1) apply a voltage across highly reflective surfaces 732 and 734 for electrostatic control of cavity length and (2) conduct electrical signals from microplatform 626 to electrical contacts located elsewhere in the interferometer and, finally, to processing electronics located external to the interferometer.

Arrangement for Applying a Voltage to Highly Reflective Surfaces.

The length of cavity 736 (gap G) can be altered by applying a voltage across reflective surfaces 732 and 734. In this context, the reflective surfaces function as electrodes of an electrostatic actuator. Since, in the illustrative embodiment, the reflective surfaces comprise metal, electrical connection to surfaces 732 and 734 is trivial.

Voltage is applied to reflective surface 734 (i.e., the "upper fixed mirror") using contacts 748B and 738. Contact 748B is an ohmic contact to layer 612 and contact 738 is an ohmic contact between layer 612 and reflective surface 734. Electrical interconnect 758 couples contact 748B to contact 750B. Contact 750B is coupled to a controlled voltage source (not depicted).

Voltage can be applied to reflective surface 732 (i.e., the "lower movable mirror) using contacts 748A or 748C. Interferometer 312 is typically arranged, however, to provide only one electrical path to reflective surface 732 for the application of a voltage. In the illustrative embodiment, that path is through contact 748A.

Through-wafer vias 740A and 740B are used to access electrical contact layer 608, which is the layer on which electrical traces reside. Vias 740A and 740B extend all the way through "upper" wafer 610 to "lower" wafer 602. More particularly, these through-wafer vias extend through layers 612, 614, 616, 618, "exposing" layer 608. Insulating layer 742 (e.g., silicon dioxide, etc.) is disposed on the sidewalls of vias 740A and 740B and layer 744 of an electrical conductor, such as aluminum, etc., is disposed on insulating layer 742. Electrical contacts 746A and 746B are formed at the base of vias 740A and 740B, respectively.

Figure 8A:
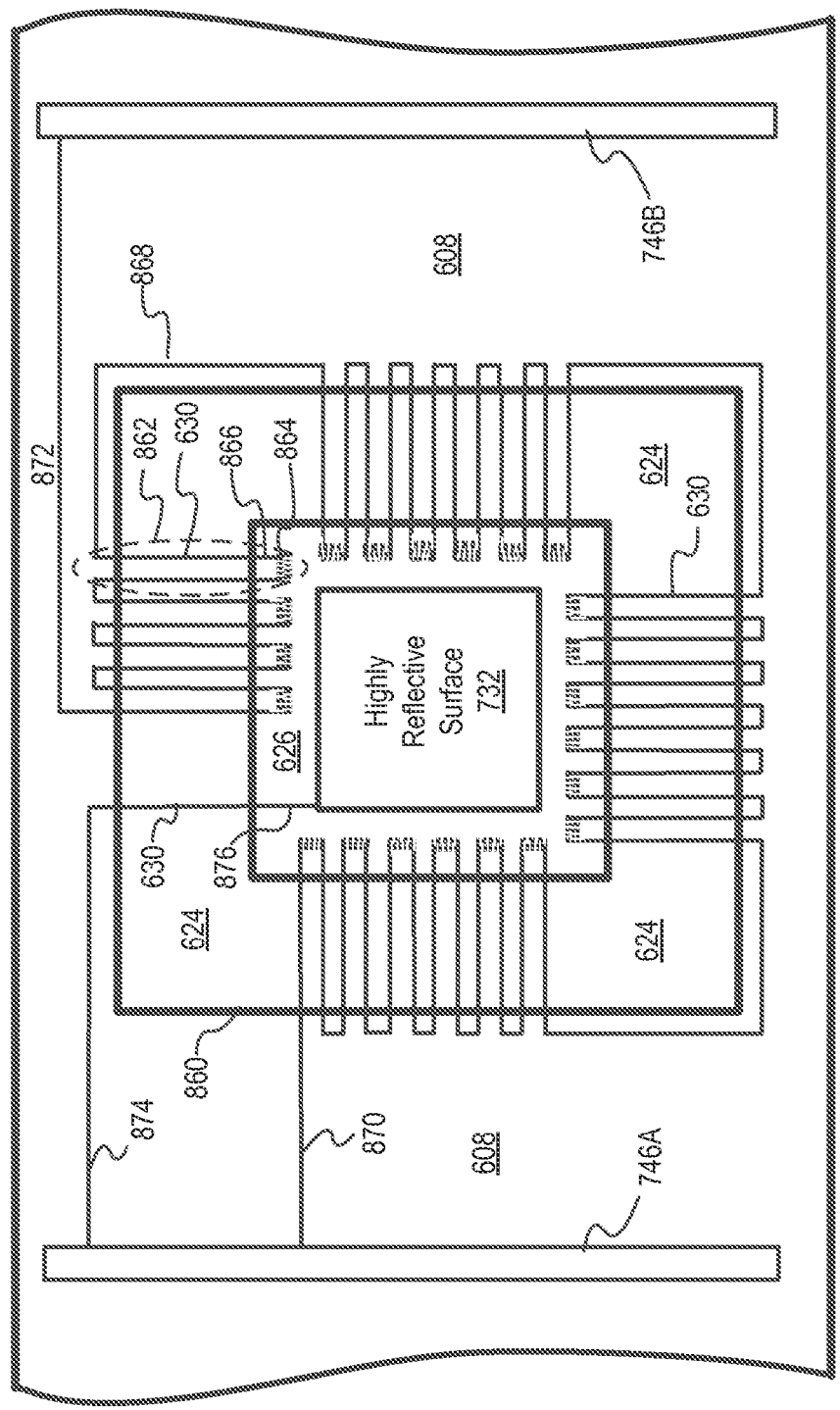
FIG. 8A depicts a cross-sectional view of the integrated Fabry-Perot interferometer shown in FIG. 6 through the line A-A in the direction shown.

As described in further detail in conjunction with FIG. 8A, in the illustrative embodiment, electrically conductive trace 874 disposed on the "upper" surface of electrical contact layer 608 electrically couples contact 746A to one nanowire 630. Electrically conductive trace 876, which is disposed on micro-platform 626, couples the one nanowire to reflective surface 732 to complete the electrical path from contact 748A. A layer of an electrically insulating material, such as silicon dioxide, is disposed between electrical contact layer 608 and the metallization. In embodiments in which metal is used for electrical conduction, a layer of insulator is disposed between the metal and the "supporting" layer to the extent needed to provide electrical insulation from underlying silicon.

In some alternative embodiments, rather than creating electrical paths via metallic traces, layer 608 is doped to provide electrically conductive paths. In such embodiments, to maintain electrical isolation between such conductive paths, layer 608 must comprise a high resistivity material, such as high resistivity silicon. As discussed further below, nanowires 630 are not metallized; rather, electrical conductivity is provided by doping the nanowires.

Arrangement for Conducting Electrical Signals from the Micro-Platform to Off-Platform Contacts and External Circuitry.

As previously mentioned, in the illustrative embodiment, detectors (partially) within micro-platform 626 are implemented as thermal detectors. Such detectors will generate a voltage when they detect heat. The voltage signals generated by the detectors are ultimately processed as part of the spectrophotometry process. To do so, such signals must be transmitted to external circuitry (e.g., for analog to digital conversion, for Fourier algorithmic processing, etc.).

Figure 8B:
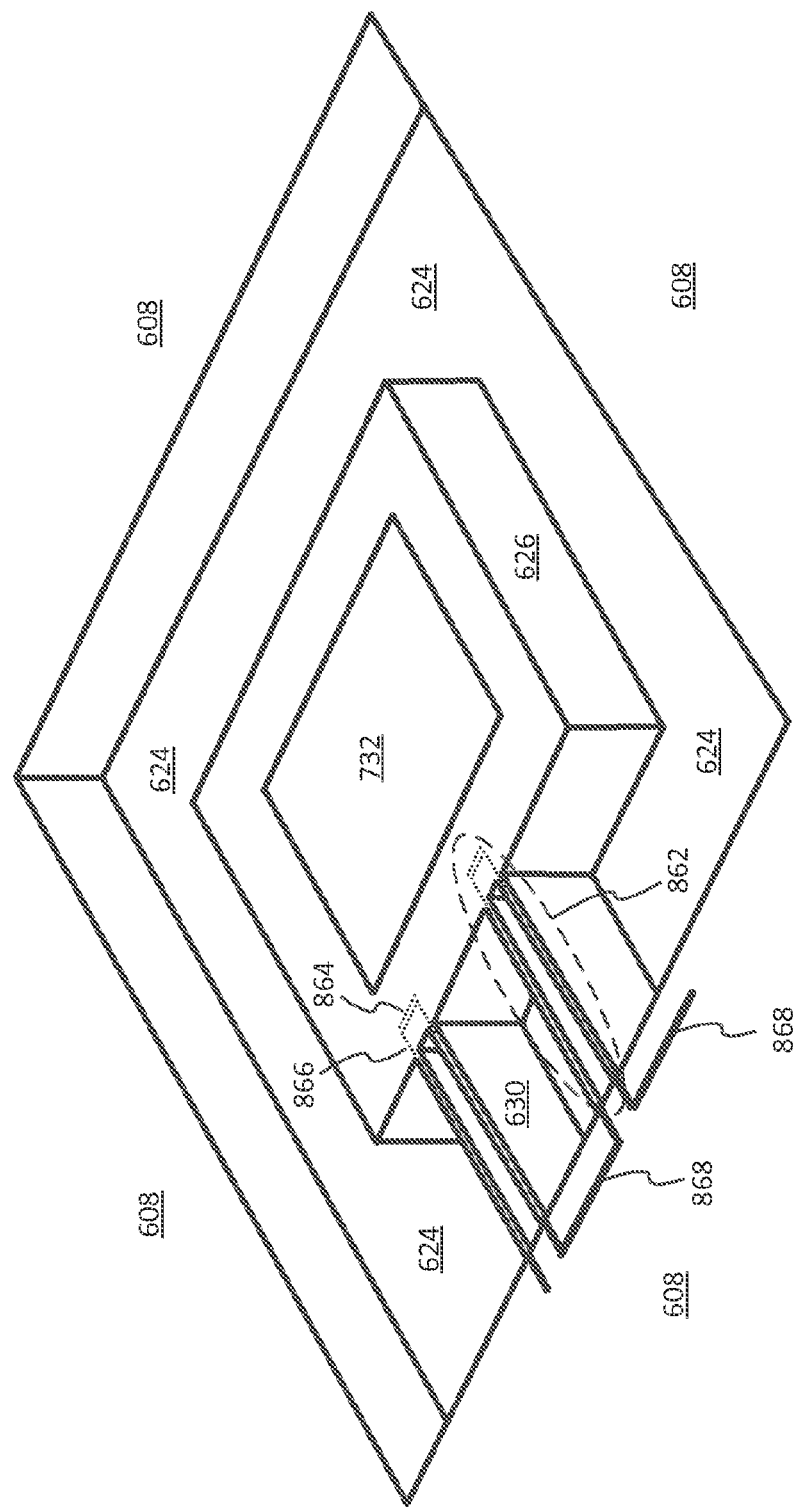
FIG. 8B depicts a perspective view of a portion of the integrated Fabry-Perot interferometer shown in FIG. 6.

The detector signals are electrically conducted off of micro-platform 626 via nanowires 630, which are described in further detail in conjunction with FIGS. 8A and 8B. Electrically conductive traces disposed on layer 608 electrically couple the signals from nanowires 630 to electrical contacts 746A and 746B located at the "base" of through-wafer vias 740A and 740B. These electrical contacts are electrically coupled to respective contacts 748A and 748C disposed "on top" of interferometer 312 in conjunction with metallization layer 744 disposed on the "right-hand" sidewall of the respective through-wafer vias. Contacts 748A and 748C are electrically coupled to contacts 750 on substrate 600, at which point the signals can be transmitted to external circuitry. Because of the preponderance of electrical traces on the "field" region of layer 608, that region is referred to herein as the "electrical contact layer".

FIG. 8A depicts a cross sectional view of interferometer 312 along the line A-A in FIG. 7 and in the direction shown. FIG. 8A is effectively a plan view of interferometer 312 with all layers above layer 608 removed.

Contacts 746A and 746B are the electrical contacts that are disposed at the base of through-wafer vias 740A and 740B (see FIG. 7), as previously discussed. Electrical traces 874 (on field region 608) and 876 (on micro-platform 626), in conjunction with a nanowire 630, place contact 746A and reflective surface 732 in electrical contact for the application of a voltage, such as for electrostatically adjusting interferometer cavity length.

A plurality of detectors 862 are formed in/on micro-platform 626. In the illustrative embodiment, the detectors are thermal detectors—in particular thermocouples—that are series-connected to form a thermopile. One end of the thermopile is electrically coupled, via metallization trace 870, to contact 746A. The other end of the thermopile is electrically coupled, via metallization trace 872, to contact 746B.

In the illustrative embodiment, each detector 862 comprises a Seebeck junction and two arms. The two arms are implemented via two nanowires 630, one of which is n-doped and the other of which is p-doped. Junction 864 is disposed in/on micro-platform 626 and is formed by appropriately doping (with p-material and n-material) the region of micro-platform 626 between the ends of two nanowires. Micro-platform 626 is also pattern-doped in the region between the end of each nanowire 630 and its respective junction 864 to create electrically conductive path 866 that places the nanowire and p-n junction in electrical contact with one another. Path 866 is doped with the same material as the associated nanowire 630. Dopant materials include, for example, phosphorus, arsenic, and boron. Electrical traces 868 disposed on electrical contact layer 608 (with an intervening layer of insulator) electrically connect detectors 862 to one another in the off platform of layer 608 to provide the series connection.

In some other embodiments, thermal detectors 862 are thermistors. The thermistors are formed by pattern-doping the active layer with one or more of phosphorus, arsenic, and boron. In yet some further embodiments, the detector is a small band-gap semiconductor junction or a high-Z thermoelectric junction. In such embodiments, the junction is formed of InAs, GaAs, InAs, HgCdTe or other appropriate semiconductor materials obtained variously through CVD deposition, sol-gel deposition, and patterned-doping processes.

FIG. 8B depicts a perspective view of micro-platform 626 and two detectors 862. For clarity, other detectors and nanowires are not depicted in FIG. 8B, it being understood that additional detectors having nanowires 630 extending from all four sides of micro-platform 626 are present, as depicted in FIG. 8A.

As shown in FIG. 8B, nanowires 630 are patterned from layer 608 and have a thickness equal to that of layer 608, but have an exceedingly small width (10 to 2000 nanometers). It is notable that in FIG. 7, nanowires 630 are illustrated with a "sawtooth" profile, similar to the manner in which a "resistor" is normally depicted. Nanowires 630 are not resistors; they are drawn in this fashion to be readily distinguishable, for example in FIGS. 5, 6B, and 7, from the unpatterned material of layer 608 and micro-platform 626.

With continued reference to FIGS. 8A and 8B, nanowires must be electrically conductive yet, at the same time, they should exhibit low thermal conductivity to keep the amount of heat that they conduct on or off micro-platform 626 to a practical minimum (for embodiments in which detectors 862 are implemented as thermal detectors). For this reason, in the illustrative embodiment, the upper surface of nanowires 630 is not metallized. That is, although such metallization would readily provide electrically conductive paths for conducting a voltage on to, or electrical signals off of, micro-platform 626, metal is an excellent conductor of heat.

The thermal conductivity of nanowire 630 is a function of the thermal energy conducted through charge carriers and lattice-energy transfer mechanisms. For silicon semiconductor nanowires, the thermal conductivity is primarily determined by phonon scattering, which is, in turn, a function of nanowire cross-section and the presence of internal scattering structures. The greater the scattering, the lower the thermal conductivity.

In accordance with some embodiments, nanowires 630 include a physical adaptation that reduces their ability to conduct heat. In some embodiments, the physical adaptation is a plurality of "scattering holes" (not depicted) to scatter phonons, thereby reducing thermal conductivity along the length of each nanowire 630. The spacing between the scattering holes on each nanowire is approximately the phonon scattering length and greater than the scattering length for electrical charge carriers (i.e., electrons or holes). In particular, the phonon scattering length in silicon (about 50 to 500 nanometers) is typically about 10× greater than the scattering length for electrical charge carriers (about 5 to 50 nanometers). The presence of these scattering holes results in an increase in the ratio of electrical conductivity to thermal conductivity of each nanowire 630. For additional disclosure concerning nanowires and other aspects of micro-platform 626, see, U.S. patent application Ser. No. 14/245,598, which is incorporated by reference herein in its entirety.

To further increase the thermal isolation of micro-platform 626, in some embodiments, a portion of support layer 624 below nanowires 630 is removed.

Fabrication.

Processing of the "Lower" Wafer 602.

Referring generally to FIGS. 6A, 6B, 7, 8A, and 8B, device layer 608 of SEMICONDUCTOR-ON-INSULATOR wafer 602 is appropriately patterned to create micro-platform 626 and the nanowires 630. The micro-platform is lithographically patterned, for example, via reactive ion etching (RIE). In the illustrative embodiment, layer 606, which is silicon dioxide, is used as an etch stop.

Micro-platform 626 is doped to form detectors 862. As previously discussed, in the illustrative embodiment, the detectors are thermal detectors, such as thermocouples. The thermocouples are formed by pattern-doping micro-platform 626 to form a Seebeck junction and nanowires 630, in alternating fashion, with n-type material and p-type material. The dopants can be one or more of phosphorus, arsenic, or boron. In some embodiments, the thermal detector is a thermistor. The thermistors are formed by doping the appropriate regions with a high-resistivity active silicon layer with one or more of phosphorus, arsenic, or boron.

Micro-platform 626 is covered by a thin (submicron) layer of a dielectric, such as silicon dioxide. Silicon dioxide can be deposited, for example, from a TEOS precursor via a low pressure chemical vapor deposition ("LPCVD") tool. In some other embodiments, the thin dielectric film is deposited from a silane/ammonia precursor in a similar CVD tool. The thin dielectric film is appropriately lithographically patterned.

In the illustrative embodiment, highly reflective surface 732 is formed by evaporating or sputtering a metal, such as aluminum, onto the topside of the thin dielectric film and appropriately patterning the metal. In some other embodiments, gold, silver, copper, dielectric sandwiches, or combinations of these materials (including aluminum) can suitably be used to form surface 732.

Highly reflective surface 732 is partially reflecting. In the illustrative embodiment in which surface 732 is formed from aluminum, the thickness thereof is in the range of about 10 to about 100 nanometers. Another film of aluminum that provides electrical contacts and interconnects with the detector is also deposited and patterned.

The portion of layer 606 underlying micro-platform 626 (i.e., layer 624) serves as a support therefor. Support layer 624 is "released" by etching into layer 604 (i.e., the handle of semiconductor-on-insulator wafer 602), creating cavity 622. Layer 606/624 serves as an etch-stop for the etch process. The etchants used are preferably anisotropic, such as, without limitation, TMAH or KOH. Alternatively, deep reactive ion etching ("DRIE") can be used can be used to create cavity 622.

In some embodiments, IR absorber 756 is formed on the "under side" of support layer 624. In embodiments in which IR absorber 756 are carbon nanotubes, they are grown, in known fashion, in a reactor using a catalyst film of iron oxide a few nanometers in thickness followed by CNT growth from a $H_2C_2$ precursor.

Processing of the "Upper" Wafer 610.

Layer 618 of an electrically insulating material, such as silicon dioxide, is formed on device layer 616 of semiconductor-on-insulator wafer 610. Layer 618 has a thickness in the range of about 50 to about 500 nanometers. Layer 618 can be formed via oxidation in a furnace. Cavity 628 is formed in layers 618 and 616 via reactive ion etching. Layer 614 is used as an etch stop. Device layer 616 and insulator layer 618 thus serves as a spacer to define the nominal "gap" (i.e., cavity length) for interferometer 312. For operation at mid- and long-wavelength infrared, the thickness of layer 616 is in the range of about 1 to about 20 microns.

A layer of aluminum, which will serve as highly reflective surface 734 (i.e., the "upper" mirror of interferometer 312), is evaporated or sputtered onto layer 614 of semiconductor-on-insulator wafer 610. In some other embodiments, films of gold, copper, multi-layer dielectrics, or combinations of these materials (including aluminum) can suitably be used to form the reflective layer. This is followed by rapid thermal annealing ("RTA") to form the ohmic contact 738 between layer 612 and surface 734. This enables a voltage to be applied to the surface 734, as required when the surface functions as an electrode for electrostatic actuation. The aluminum film covering other portions of layer 616 (i.e., outside of cavity 628) is removed by chemical/mechanical polishing ("CMP").

Through-wafer vias 740A and 740B are formed using, for example, DRIE, and are then coated with a film of a dielectric material, such as silicon dioxide, etc. A film of metal, such as aluminum, is deposited on the dielectric material in the vias and then patterned. This additional film is used to form the electrical connection with the detectors and highly reflective surface 732 on micro-platform 626.

Bonding the First and Second Wafers Together.

Wafers 602 and 610, after processing as described above, are aligned and bonded together at interface 752 using one or more of anodic, direct semiconductor-to-semiconductor, cement, or eutectic alloy bonding processes. The bonded wafers are then sawed into individual die, which are bonded at interface 754, to substrate 600. In some embodiments, this bonding is implemented with an electrically conductive epoxy perform. In the illustrative embodiment, substrate 600 is a ceramic header with appropriately patterned electrical pins and interconnects. In some other embodiments, substrate 600 is another suitable material, such as epoxy, very high-resistivity silicon, etc. In the illustrative embodiment, the integrated structure (within a packaging header) is wired to bonding pads 750 via an ultrasonic wire bonder.

Figure 9:
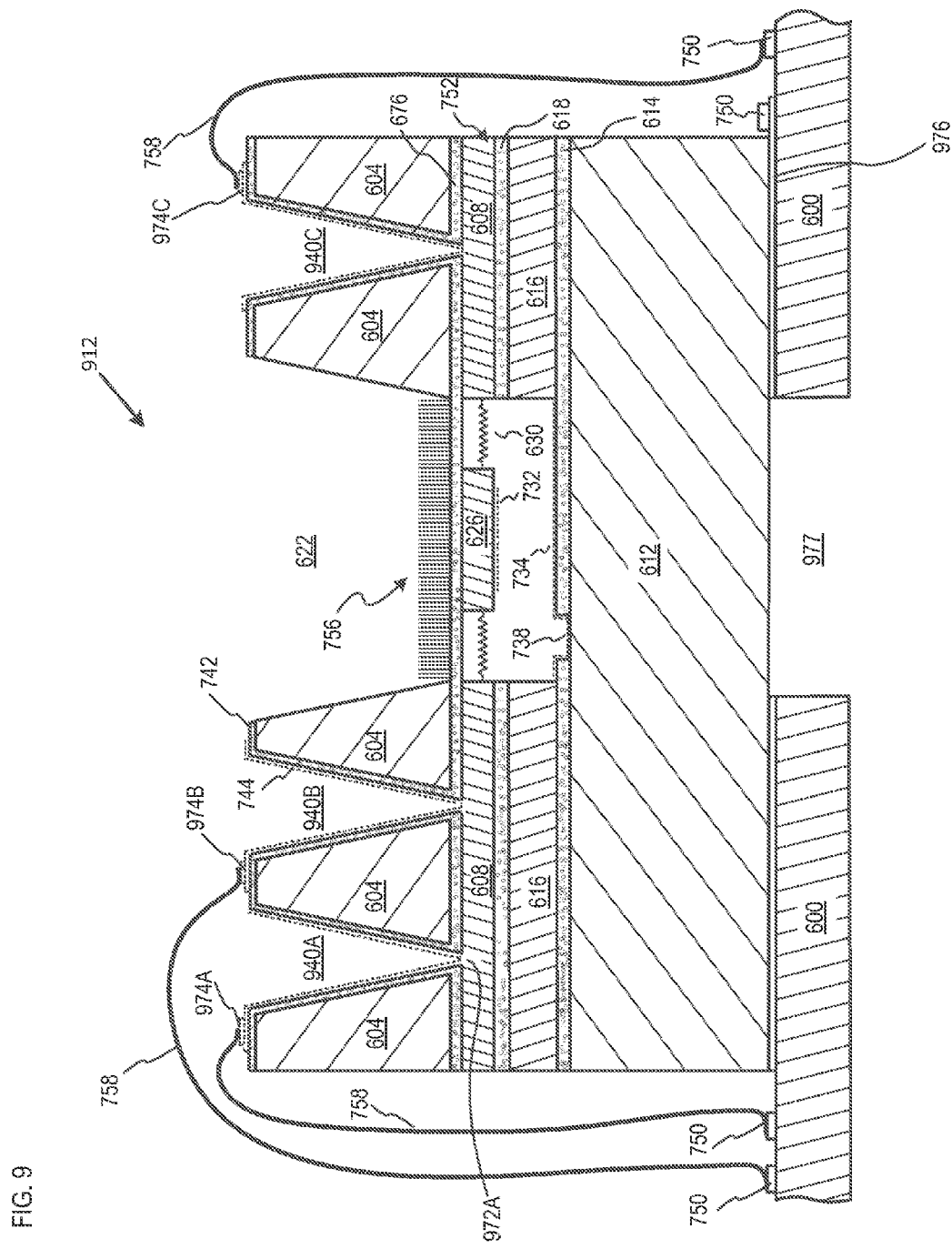
FIG. 9 depicts a cross-section view of an integrated Fabry-Perot interferometer in accordance with a second embodiment of the present invention.

FIG. 9 depicts integrated Fabry-Perot interferometer 912, which is a variation of integrated Fabry-Perot interferometer 312. In this embodiment, the placement of wafer 602 and wafer 610 (FIG. 6A) is reversed such that the movable mirror is situated "above" the fixed mirror. That is, micro-platform 626 and highly reflective surface 732 are disposed "above" highly reflective surface 734. Interferometer 912 has the same basic structure as interferometer 312, being based on two semiconductor-on-insulator wafers and a ceramic, etc., substrate.

Integrated Fabry-Perot interferometer 912 includes three vias 940A, 940B, and 940C, which all provide electrical access to electrical connections (that ultimately connect to micro-platform 626) on layer 608. Contact 750 on hermetic seal 976 and ohmic contact 738 provide electrical connection to highly reflective layer 734. An aluminum film at interface 752 is patterned to provide electrical connection between appropriate nanowires 630 and respective vias 940A, 940B, and 940C.

In this embodiment, light enters the interferometer through region 977, thereby ensuring that the light reaches interferometer cavity 732 before it encounters IR absorber 756. In some other less preferred embodiments, light enters via cavity 622, thereby encountering IR absorber 756 before reaching interferometer cavity 732. If light enters via cavity 622, the spectral finesse of interferometer 912 is likely to be degraded.

The same techniques that were used to fabricate interferometer 312 are used to fabricate interferometer 912. However, for interferometer 912, IR absorber 756 is formed after through-wafer vias 940A, 940B, and 940C.

Figure 10A:
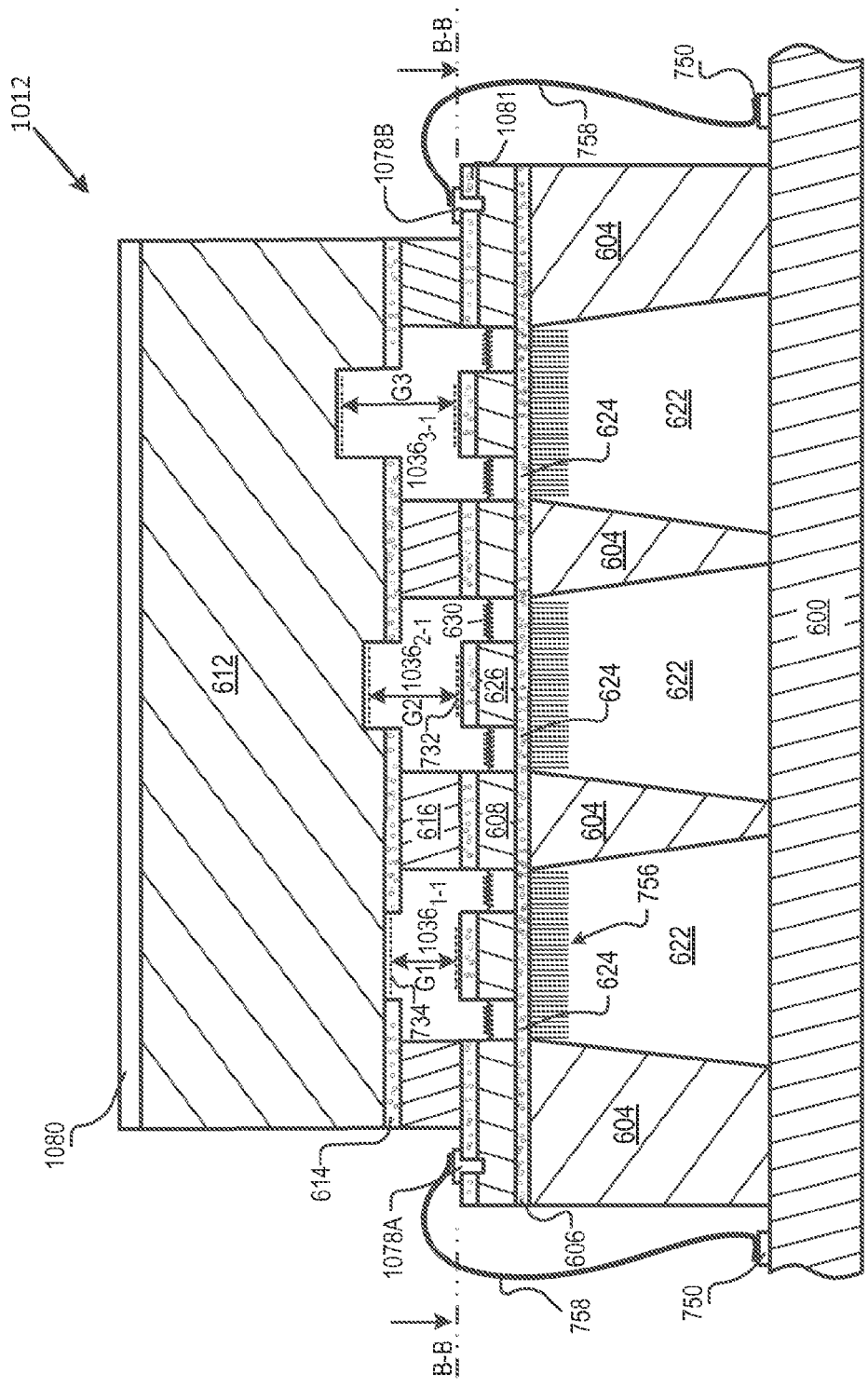
FIG. 10A depicts a cross-sectional view of an integrated Fabry-Perot interferometer in accordance with a third embodiment of the present invention.
Figure 10B:
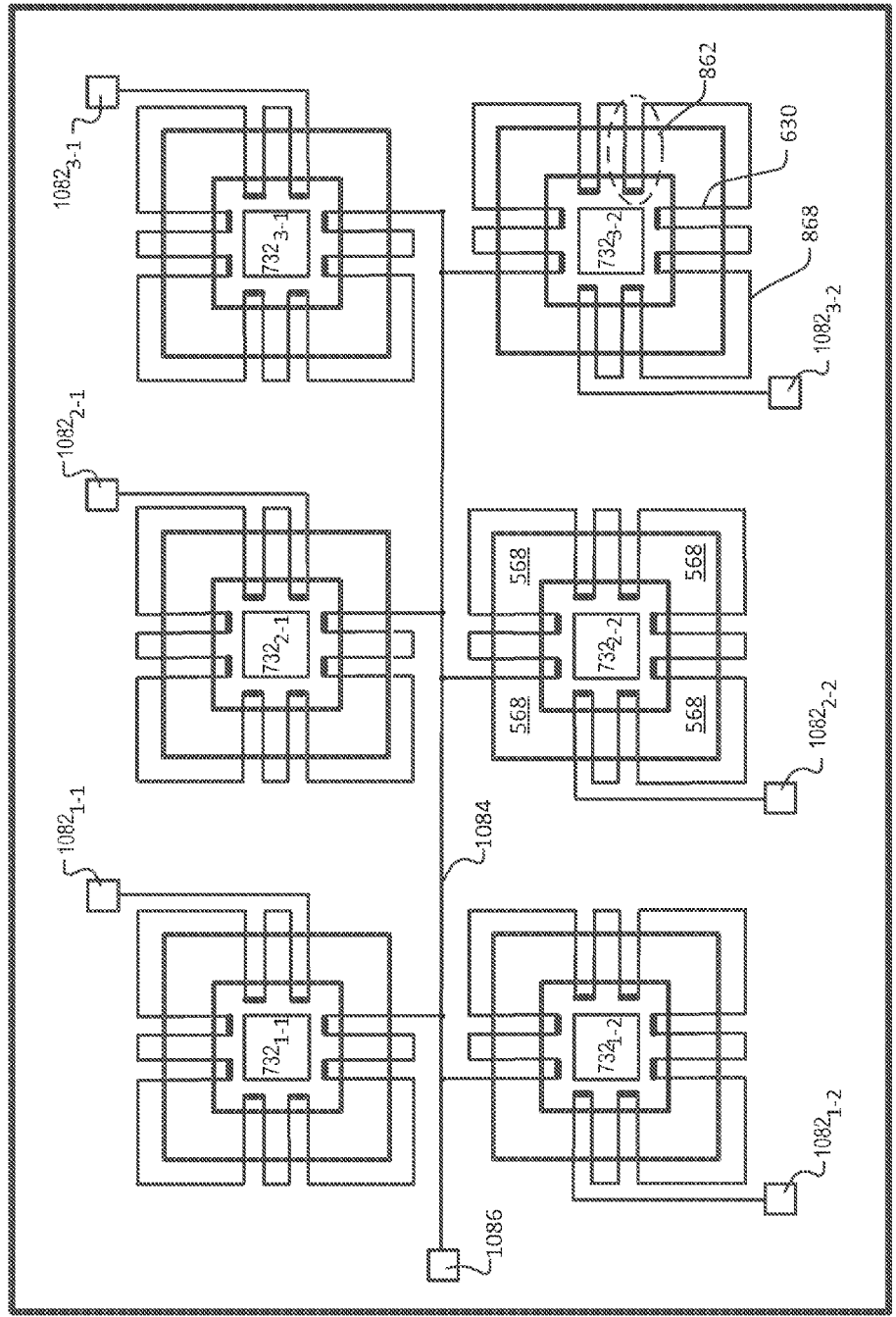
FIG. 10B depicts a cross-sectional view of the integrated Fabry-Perot interferometer shown in FIG. 10A through the line B-B in the direction shown.

FIGS. 10A and 10B depict integrated Fabry-Perot interferometer 1012, which is another variation of integrated Fabry-Perot interferometer 312. In this embodiment, cavity length is fixed. Interferometer 1012 includes multiple cavities, each tuned to filter a different selected wavelength based on cavity length.

As depicted in FIG. 10B, interferometer 1012 includes six cavities, three of which: $1036_{1-1}$, $1036_{2-1}$, $1036_{3-1}$, are visible in FIG. 10A. Cavity $1036_{1-1}$ has a cavity length of G1, cavity $1036_{2-1}$ has a cavity length of G2, and cavity $1036_{3-1}$ has a cavity length of G3. Each cavity functions as a discrete interferometer in the manner previously discussed, wherein detectors 862 (FIG. 10B) within each micro-platform generate a voltage in response to heating and electrically conducting nanowires 630 conduct the detector signals off-platform. As in other embodiments depicted, all structures external to each micro-platform 626 are effectively an isothermal reference mass. The thermocouple arrays in this embodiment provide sensitivity for thermal sensing with incident radiation wavelengths longer than typically 2 microns. IR absorber 756 enhances absorption of IR radiation in micro-platform 626.

Referring to FIG. 10B, the six arrays of detectors 862 associated with the six cavities are electrically connected to a common first interconnect 1084. The first interconnect is electrically coupled to electrical contact 1086. This arrangement simplifies the interconnection for detector readout. Electrical contact 1086 couples to electrical contact 1078A disposed on layer 1081. Electrical contact 1078A is coupled to a first electrical contact 750 on substrate 600.

Each array of detectors 862 has its own unique second electrical contact for readout: $1082_{i,j}$, wherein i=1, 3 and j=1, 3. Each second electrical contact $1082_{i,j}$ is electrically connected to electrical contact 1078B disposed on layer 1081. Electrical contact 1078B is coupled to a second electrical contact 750 on substrate 600. Light is pulsed sequentially into the various cavities. This configuration permits a parallel simultaneous readout of signals from all detectors 862 in the array via electrical contacts $1082_{i,j}$.

Referring to FIG. 10A, insulator layer 1081 is disposed on layer 608. That is, an additional insulator layer (e.g., silicon dioxide, etc.) is added to the device layer of the lower starting semiconductor-on-insulator wafer. Layer 1081 provides electrical isolation between the interconnections that are patterned onto electrical contact layer 608. This layer also improves the finesse of interferometer 1012 by reducing the penetration of the evanescent wave to the detector. Anti-reflection layer 1080 is disposed on layer 612 to reduce reflection of the incident radiation. In some embodiments, layer 1080 is a quarter-wave thickness of a single dielectric film or a sandwich of multiple dielectrics.

The same techniques that were used to fabricate interferometer 312 are used to fabricate interferometer 1012.

The "pedestals" defined by portions of layer 608, layer 1081, and layer 616 serve as both an isothermal reference for thermal detectors in the micro-platforms 626 and as a support for electrical interconnects. The differences in cavity length between the cavities result from etching a different distance into layer 612. The pedestals also effectively extend the two "inner pedestals" of layer 604 that support layer 606. This helps to reduce or eliminate variations in the gaps in each cavity due to bowing of the layers 604 and 612.

Although the embodiment of integrated Fabry-Perot interferometer 1012 depicted in FIGS. 10A and 10B has six interferometric cavities, in some other embodiments, interferometer 1012 can include fewer or more than six such cavities.

It is to be understood that although the disclosure teaches many examples of embodiments in accordance with the present teachings, many additional variations of the invention can easily be devised by those skilled in the art after reading this disclosure. As a consequence, the scope of the present invention is to be determined by the following claims.

What is claimed:

1. An apparatus comprising an integrated Fabry-Perot interferometer, wherein the integrated Fabry-Perot interferometer comprises:
   a first highly reflective surface and a second highly reflective surface spaced apart from one another defining a first interferometer cavity;
   a first micro-platform, wherein the first highly reflective surface is supported by the first micro-platform, and wherein the first micro-platform is disposed on a first side of a support layer, wherein the support layer is supported at its ends so that the support layer and any structure supported thereby is movable, and further wherein the first micro-platform is positioned to receive electromagnetic radiation exiting the first interferometer cavity through the first highly reflective surface; and
   a plurality of detectors disposed at least partially in or on the first micro-platform, wherein the detectors are capable of generating an electrical signal responsive to the electromagnetic radiation received by the first micro-platform.

2. The apparatus of claim 1 wherein the first highly reflective surface and the second highly reflective surface are electrically conductive, and further comprising electrical pathways that independently electrically couple the first highly reflective surface and the second highly reflective surface with a controlled voltage source.

3. The apparatus of claim 1 wherein at least some of detectors of the plurality thereof are thermal detectors.

4. The apparatus of claim 1 wherein at least some of the thermal detectors are series connected with one another, providing a thermopile.

5. The apparatus of claim 1 and further comprising an IR absorber for enhancing absorption of infrared radiation, wherein the IR absorber is disposed on a second side of the support layer.

6. The apparatus of claim 1 wherein the first highly reflective surface is supported by a device layer of a first pattered semiconductor-on-insulator wafer and the second highly reflective surface is disposed on a buried oxide layer of a second patterned semiconductor-on-insulator wafer.

7. The apparatus of claim 6 wherein a length of the first interferometer cavity, in a quiescent state, is equal to A minus B, wherein:
  A=a thickness of a device layer of the second patterned wafer+a thickness of an oxide layer disposed between the device layer of the second patterned wafer and the device layer of the first patterned wafer; and
  B=a thickness of the first highly reflective surface+a thickness of the second highly reflective surface+a thickness of material that is disposed between the device layer of the first patterned wafer and the first highly reflective surface.

8. The apparatus of claim 1 wherein the support layer is a portion of a buried oxide layer of a first patterned semiconductor-on-insulator wafer, and wherein the first highly reflective surface is supported by a first portion of a device layer of the first pattered semiconductor-on-insulator wafer.

9. The apparatus of claim 8 wherein the first micro-platform is spaced apart from and surrounded by an electrical contact layer, wherein the electrical contact layer has electrically conductive traces disposed thereon, and wherein the first micro-platform is the first portion of the device layer and the electrical contact layer is a second portion of the device layer.

10. The apparatus of claim 1 further comprising:
  a light source for generating electromagnetic energy in at least one of the visible range and the infrared range;
  wireless telecommunications components that communicate information obtained by the integrated Fabry-Perot interferometer to one or more external devices or circuits;
  a sampling region; and
  a housing, wherein the housing contains the integrated Fabry-Perot spectrophotometer, the light source, the wireless telecommunications components, and is configured to provide the sampling region.

11. The apparatus of claim 10 further comprising a processor that processes the information obtained from the integrated Fabry-Perot interferometer.

12. The apparatus of claim 11 wherein the processor is disposed in the housing.

13. The apparatus of claim 10 wherein the wireless telecommunications components comprises an RF antenna.

14. The apparatus of claim 13 wherein the apparatus further comprises circuitry and devices for operating the antenna to harvest energy from an external source.

15. The apparatus of claim 1 further comprising a processor that:
  a) processes information sourced from the integrated Fabry-Perot interferometer to obtain a spectral analysis of electromagnetic radiation that enters the integrated Fabry-Perot interferometer after interrogating an analyte within a medium, the spectral analysis comprising electromagnetic-radiation intensity as a function of wavelength over a range of wavelengths;
  b) compares the spectral analysis with reference data stored in processor-accessible memory, wherein the reference data provides intensity-versus-wavelength data for the analyte as a function of concentration; and
  c) determines, from the comparison, the concentration of the analyte in the medium.

16. The apparatus of claim 15 wherein the analyte is glucose and the medium is blood.

17. An apparatus comprising an integrated Fabry-Perot interferometer, wherein the integrated Fabry-Perot interferometer comprises:
  a first highly reflective surface and a second highly reflective surface spaced apart from one another defining a first interferometer cavity;
  an electrical contact layer, wherein the electrical contact layer comprises a non-metallic material having electrically conductive traces disposed thereon;
  a first micro-platform, wherein the first highly reflective surface is supported by the first micro-platform, and wherein the first micro-platform is spaced apart from and surrounded by the electrical contact layer and is positioned to receive electromagnetic radiation exiting the first interferometer cavity through the first highly reflective surface; and
  a plurality of detectors disposed at least partially in or on the first micro-platform, wherein the detectors are capable of generating an electrical signal responsive to the electromagnetic radiation received by the first micro-platform.

18. The apparatus of claim 17 wherein the electrically conductive traces on the electrical contact layer facilitate electrical coupling of the detectors to electrical circuits or devices that are external to the integrated Fabry-Perot interferometer.

19. The apparatus of claim 17 further comprising a plurality of nanowires, wherein the plurality of nanowires electrically couple, to the electrically conductive traces on the electrical contact layer, electrically conductive structures disposed in or on or supported by the first micro-platform.

20. The apparatus of claim 19 wherein the electrically conductive structures are selected from the group consisting of a Seebeck junction, a p-n junction, and the first highly reflective surface.

21. The apparatus of claim 19 wherein the first micro-platform, the plurality of nanowires, and the electrical contact layer all comprise the same non-metallic material and all have the same thickness.

22. The apparatus of claim 19 wherein a thermal conductivity of the plurality of nanowires is sufficiently low to enable the first micro-platform to be effectively thermally isolated from the electrical contact layer, such that the electrical contact layer serves as a reference temperature for the plurality of detectors, which are thermal detectors.

23. The apparatus of claim 19 wherein adjacent nanowires in the plurality thereof are paired to one another and, within each pair, are coupled to one another via a Seebeck junction, each pair of nanowires and the coupling Seebeck junction collectively defining a respective one of the detectors of the plurality thereof.

24. The apparatus of claim 17, wherein the integrated Fabry-Perot interferometer further comprises:
  a third highly reflective surface and a fourth highly reflective surface spaced apart from one another defining a second interferometer cavity;

a second micro-platform, wherein the third highly reflective surface is supported by the second micro-platform, and wherein the second micro-platform is positioned to receive electromagnetic radiation exiting the second interferometer cavity through the third highly reflective surface; and a plurality of detectors disposed at least partially in or on the second micro-platform, wherein the detectors are capable of generating an electrical signal responsive to the electromagnetic radiation received by the second micro-platform.

25. The apparatus of claim 24 wherein a distance between the first and second highly reflective surfaces defines a length of the first interferometer cavity and a distance between the third and fourth highly reflective surfaces defines a length of the second interferometer cavity, and wherein the length of the first interferometer cavity and the length of the second interferometer cavity are different from one another.

\* \* \* \* \*